United States Patent
Nakayama et al.

(10) Patent No.: US 9,400,282 B2
(45) Date of Patent: Jul. 26, 2016

(54) METHOD FOR QUANTIFYING PROTEIN

(75) Inventors: Keiichi Nakayama, Fukuoka (JP); Masaki Matsumoto, Fukuoka (JP)

(73) Assignee: KYUSHU UNIVERSITY, NATIONAL UNIVERSITY CORPORATION, Fukuoka-shi (JP)

( * ) Notice: Subject to any disclaimer, the term of this patent is extended or adjusted under 35 U.S.C. 154(b) by 615 days.

(21) Appl. No.: 13/383,925

(22) PCT Filed: Jul. 16, 2010

(86) PCT No.: PCT/JP2010/062124
§ 371 (c)(1),
(2), (4) Date: Mar. 7, 2012

(87) PCT Pub. No.: WO2011/007884
PCT Pub. Date: Jan. 20, 2011

(65) Prior Publication Data
US 2012/0156710 A1 Jun. 21, 2012

(30) Foreign Application Priority Data
Jul. 17, 2009 (JP) ................................ 2009-169045

(51) Int. Cl.
*G01N 33/68* (2006.01)
(52) U.S. Cl.
CPC .................................. *G01N 33/6848* (2013.01)
(58) Field of Classification Search
None
See application file for complete search history.

(56) References Cited

FOREIGN PATENT DOCUMENTS

| WO | WO 2007/140291 | 12/2007 |
|---|---|---|
| WO | WO 2008/022205 | 2/2008 |

OTHER PUBLICATIONS

Stone et al. (Identification of proteins based on MS/MS spectra and location of posttranslational modifications, Methods Mol Biol. 2007; 386: 57-77).*
Supplementary European Search Report mailed Mar. 13, 2013 in counterpart application No. 10799942.7 (7 pages).
Leroi V. DeSouza et al.: "Multiple Reaction Monitoring of mTRAQ-Labeled Peptides Enables Absolute Quantification of Endogenous Levels of a Potential Cancer Marker in Cancerous and Normal Endometrial Tissues", Journal of Proteome Research, Jul. 17, 2008, pp. 3525-3534.
Geraldine M. Walsh et al.: "Implementation of a data repository-driven approach for targeted proteomics experiments by multiple reaction monitoring", Elsevier, Journal of Proteomics, 2008 (15 pages).
David R. Barnridge et al.: "Absolute Quantification of the Model Biomarker Prostate-Specific Antigen in Serum by LC-MS/MS Using Protein Cleavage and Isotope Dilution Mass Spectrometry", Journal of Proteome, vol. 3, No. 3, 2004, pp. 644-652.
Dariusz J. Janecki et al.: "A multiple reaction monitoring method for absolute quantification of the human liver alcohol dehydrogenase ADH1C1 isoenzyme", *Analytical Biochemistry*, vol. 369, No. 1, Oct. 1, 2007, pp. 18-26.
Viveka Mayya et al.: "Absolute Quantification of Multisite Phosphorylation by Selective Reaction Monitoring Mass Spectrometry", *Molecular and Cellular Proteomics*, vol. 5, No. 6, Jun. 2006, pp. 1146-1157.
Jianru Stahl-Zeng et al.: "High Sensitivity Detection of Plasma Proteins by Multiple Reaction Monitoring of N-Glycosites", *Molecular and Cellular Proteomics*, vol. 6, No. 10, Oct. 2007, pp. 1809-1817.
Shao-En Ong et al.: "Stable Isotope Labeling by Amino Acids in Cell Culture, SILAC, as a simple and Accurate Approach to Expression Proteomics", *Molecular and Cellular Proteomics*, vol. 1, No. 5, 2002, pp. 376-386.
Steven P. Gygi et al.: "Quantitative analysis of complex protein mixtures using isotope-coded affinity tags", Nature Biotechnology, vol. 17, No. 10, Oct. 1999, pp. 994-999.
Hwee Tong Tan et al.: "Quantitative and Temporal Proteome Analysis of Butyrate-treated Colorectal Cancer Cells", *Molecular and Cellular Proteomics*, vol. 7, No. 65, 2008, pp. 1174-1185.
Vinzenz Lange et al.: "Targeted quantitative analysis of *Streptococcus pyogenes* virulence factors by multiple reaction monitoring", *Molecular and Cellular Proteomics*, vol. 7, No. 8, 2008, pp. 1489-1500.
Vinzenz Lange et al.: "Selected reaction monitoring for quantitative proteomics: a tutorial", *Molecular and Cellular Proteomics*, vol. 4, No. 222, Jun. 1, 2008, pp. 1-14.
Supplemental European Search Report mailed Mar. 18, 2013 in counterpart application No. 10799942.7 (7 pages).
Summons to Oral Proceedings dated Apr. 10, 2015 for European Patent Application No. 10799942.7.
The FASEB Journal, Nov. 1, 2005, vol. 19, No. 13, pp. 1809-1821; Arsalan S. Haqqani, et al. "Characterization of vascular protein expression patterns in cerebral ischemia/reperfusion using laser capture microdissection and ICAT-nanoLC-MS/MS".

* cited by examiner

*Primary Examiner* — Suzanne M Noakes
*Assistant Examiner* — Jae W Lee
(74) *Attorney, Agent, or Firm* — Kratz, Quintos & Hanson, LLP

(57) ABSTRACT

A method for measuring the absolute amount of a target protein contained in a protein mixture, including the steps of:
(A) fragmenting the sample containing the target protein and labeling with a stable isotope X;
(B) adding a known amount of an internal standard that is prepared by fragmenting a standard protein that is identical to the target protein, and labeling with a stable isotope Y;
(C) placing the sample in an LC-MS/MS device and performing multiple reaction monitoring (MRM) analysis using MRM transitions selected for the internal standard; and
(D) identifying a peptide derived from the target protein (a target peptide) that shows the same retention time as a peptide derived from the internal standard (an internal standard peptide), and quantifying the target protein in the test sample by comparing the peak area of the internal standard peptide with the peak area of the target peptide.

17 Claims, 3 Drawing Sheets

A

B

METHOD FOR QUANTIFYING PROTEIN

TECHNICAL FIELD

The present invention relates to a method for quantifying protein by a multiple reaction monitoring (MRM) method. More specifically, the present invention relates to a method useful for measuring the absolute amount of a target protein contained in a protein mixture, such as a biological sample.

BACKGROUND ART

The homeostasis of life is maintained by a network composed of numerous proteins. Since various diseases can be perceived as a failure of homeostasis, the amount of each protein present in a living body can be used as a biomarker for elucidation of the molecular mechanism or diagnosis of diseases, or as a criterion for therapeutic prognosis. Although both high comprehensiveness and high sensitivity are required in protein detection and quantification to achieve this purpose, there is presently no technique that is sufficient for practical use.

Examples of known high-sensitivity protein detection methods include immunochemical methods, such as western blotting utilizing antibodies specific to individual proteins. However, in immunochemical methods, the acquisition of specific antibodies is a prerequisite, and the obtained results greatly depend on the quality of the antibody used. Furthermore, in order to detect plural proteins by an immunochemical method, all antibodies against individual proteins must be prepared, and analysis must be repeated using each individual antibody. However, making such comprehensive analysis is substantially impossible.

Examples of known methods for comprehensive analysis of proteins include proteome analysis methods using a mass spectrometer as basic technology. However, according to conventional proteome analysis methods, detecting trace proteins is extremely difficult. For example, two-dimensional electrophoresis, which is a typical proteomic expression analysis method, can only detect proteins with high expression levels. Even with the use of quantitative shotgun proteomics, which is a combination of LC-MS/MS with stable isotope labeling (SILAC, ICAT, iTRAQ), the number of proteins that can be detected is only several hundreds to about 3,000. When the number of detections is within such a range, detecting or quantifying trace proteins is impossible (see Non-patent Literature (NPL) 1 to 3). Furthermore, the purpose of these methods is generally relative quantification, rather than absolute quantification, of proteins. It is thus difficult to derive a quantitative relationship between proteins by comparing quantitative values of the proteins individually obtained in different research and testing laboratories by using such methods.

As a method for overcoming the problem of the conventional protein quantification analysis, multiple reaction monitoring (MRM) (also referred to as "selective reaction monitoring" (SRM)), which has been used for quantitative analysis of low molecular compounds, has been proposed to be used for peptide quantification (see Non-patent Literature (NPL) 4). However, obtaining MS/MS spectral information on the target peptide beforehand is necessary to perform MRM.

In general, the number of peptides generated from one protein by enzymatic digestion, etc., may range from several tens to several hundreds. Selection of the target peptide to be subjected to MRM is a very important step in specifying the sensitivity of this method. At present, the selection of the target peptide for MRM is made by utilizing a measured spectrum obtained by shotgun proteome analysis; or depends on a method of theoretical estimation under specific conditions.

However, because the actual spectrum data of trace proteins is rarely obtained, and theoretical estimation does not always guarantee the selection of highly sensitive peptides, the development of a method of efficiently selecting an MRM target peptide is necessary to perform comprehensive high-sensitivity MRM.

Thus, the MRM method is currently recognized only as a methodology for reviewing and confirming the results obtained by shotgun proteome analysis, etc., and is not expected to be used as a large-scale screening method.

CITATION LIST

Non-Patent Literature

NPL 1: Ong S E, Blagoev B, Kratchmarova I, Kristensen D B, Steen H, Pandey A, Mann M. Mol Cell Proteomics. 1(5): 376-86, 2002
NPL 2: Gygi S P, Rist B, Gerber S A, Turecek F, Gelb M H, Aebersold R. Nat Biotechnol. 17(10): 994-9, 1999
NPL 3: Tan H T, Tan S, Lin Q, Lim T K, Hew C L, Chung M C. Mol Cell Proteomics. 7(6): 1174-85, 2008
NPL 4: Lange V, Malmstrom J A, Didion J, King N L, Johansson B P, Schafer J, Rameseder J, Wong C H, Deutsch E W, Brusniak M Y, Buhlmann P, Bjorck L, Domon B, Aebersold R. Mol Cell Proteomics. 7(8): 1489-500, 2008
NPL 5: Lange V, Picotti P, Domon B, Aebersold R. Mol Syst Biol. 2008; 4:222

SUMMARY OF INVENTION

Technical Problem

In view of the current state and problems of the protein quantification techniques, an object of the present invention is to provide a method for measuring the absolute amounts of target proteins contained in a biological sample that is a mixture of various proteins, and more preferably a method that can measure the absolute amounts of target proteins at a high speed. According to the method of the present invention, the MRM method, which has been used as a means for analyzing a specific protein, can be converted into an ultra-high-sensitivity large-scale protein analysis method by utilizing genome information resources that have recently become abundant.

Solution to Problem

MRM is a method for specifically quantifying a specific component contained in a complicated sample by providing a combination of two mass filters (MRM transitions: a combination of mass (m/z) filters Q1 and Q3), i.e., a mass filter (Q1) through which an ion having a specific mass (a peptide herein) can be passed, and a mass filter (Q3) through which fragments generated by gas collision-induced dissociation (CID) can be passed, and detecting an ion (a peptide) that can pass through these two mass filters (Non-patent Literature (NPL) 5).

MRM analysis is expected as a new technique that can solve the broad dynamic range problem of the proteome. However, to perform MRM analysis, it is necessary to know beforehand mass data (MS/MS spectrum) of the fragments generated by CID of the target peptide. Since MS/MS spectrum data obtained by shotgun proteomics analysis are generally used as such information, MRM analysis of trace proteins that cannot be detected by shotgun analysis is difficult. As a means for solving these problems, in particular the latter problem, the present invention was accomplished.

The present invention includes the following embodiments:

Item 1. A method for identifying and quantifying target proteins in a test sample containing plural kinds of proteins, the method comprising:

(A) a step of fragmenting the sample containing the target proteins and labeling with a stable isotope X;

(B) a step of adding, to the sample obtained in step (A), known amounts of internal standards that are prepared by fragmenting standard proteins that are identical to the target proteins and labeling the fragmented-standard proteins with a stable isotope Y;

(C) a step of placing the sample obtained in step (B) in an LC-MS/MS device, and performing multiple reaction monitoring (MRM) analysis using MRM transitions selected for the internal standards; and (D) a step of identifying, in the MRM chromatogram detected in step (C), peptides derived from the target proteins (target peptides) that show the same retention time as peptides derived from the internal standards (peptides of the internal standards), and quantifying the target proteins in the test sample by comparing the peak areas of the peptides of the internal standards with the peak areas of the target peptides.

Item 2. The method according to Item 1, wherein the MRM transitions are selected by a method comprising:

(1) a step of fragmenting the standard proteins that are identical to the target proteins and labeling with a stable isotope Y to prepare internal standards;

(2) a step of placing the internal standards obtained in step (1) in the LC-MS/MS device and determining the peptide ion intensities of fragments corresponding to the peptides derived from the standard proteins;

(3) a step of selecting two or more fragment ions that have high ionic intensity per peptide, determining the average intensities of two or more fragment ions, and selecting two or more kinds of peptides in descending order of the average intensity so as to select as MRM transitions based on the peptides.

Item 3. The method according to Item 1 or 2, wherein step (C) or (D) is performed based on a calibration reference table of the standard proteins.

Item 4. The method according to Item 3, wherein the calibration reference table of each standard protein is prepared by a method comprising:

(a) a step of fragmenting a known amounts of the standard protein and labeling with the stable isotope Y to prepare an internal standard;

(b) a step of placing the internal standard obtained in step (a) in the LC-MS/MS device and performing multiple reaction monitoring (MRM) analysis using the MRM transitions selected for the internal standard;

(c) selecting, in the MRM chromatogram, two or more kinds of peptides from the detected peptides in descending order of sensitivity, and listing the peptides with the retention time thereof;

(d) storing the list prepared in step (c) for use as the calibration reference table of the standard protein.

Item 5. The method according to Item 4, wherein steps (a) to (d) are repeated using two or more standard proteins so as to prepare and store calibration reference tables of the standard proteins, thus constructing a standard protein library.

Advantageous Effects of Invention

First, according to the present invention, peptide fragments obtained by digestion treatment of proteins are quantified, and proteins are not directly quantified. Accordingly, the quantification is not affected by the solubility of protein molecules, and proteins having various chemical properties can be treated in the same manner.

Secondly, according to the method of the present invention, a mass spectrometer is used for the measurement. Accordingly, proteins in the amount of several fmol can be quantified.

Thirdly, concurrent use of internal standard peptides corresponding to each of plural target proteins enables quantification of each of plural target proteins in one analysis.

BRIEF DESCRIPTION OF DRAWINGS

FIG. 1A shows the results of LC-MS/MS analysis of PFTS (mTRAQ-117-labeled $p27^{Kip1}$ digest) in data-dependent automatic MS/MS acquisition mode. The horizontal axis represents time (min), and the vertical axis represents the strength (cps). However, specific numerals themselves are not particularly relevant to the invention. FIG. 1B shows the results obtained by database-searching the data obtained in FIG. 1A, using MASCOT and ProteinPilot, to select MRM transitions; and actually subjecting PFTS (mTRAQ-117-labeled $p27^{Kip1}$ digest) as a sample to MRM analysis using the selected MRM transitions. Two peptides with strong signals (arrows) were selected as quantification transitions. In FIG. 1B, the horizontal axis represents time (min), and the vertical axis represents intensity (cps). However, specific numerals themselves are not particularly relevant to the invention.

FIG. 4A shows a chromatogram of the MRM analysis. The horizontal axis represents time (minute), and the vertical axis represents intensity (cps). However, specific numerals themselves are not particularly relevant to the invention. FIG. 4B shows the amount of $p27^{Kip1}$ contained in each of the cell extracts (control cells (Mock), knockdown cells (Skp2 KD 1-2 cells), and knockdown cells (Skp2 KD 3-10 cells)) (20 μg each). In FIG. 4A, arrow a indicates a peak derived from the sample, whereas arrow b indicates a peak derived from the internal standard.

DESCRIPTION OF EMBODIMENTS

Figure 1:
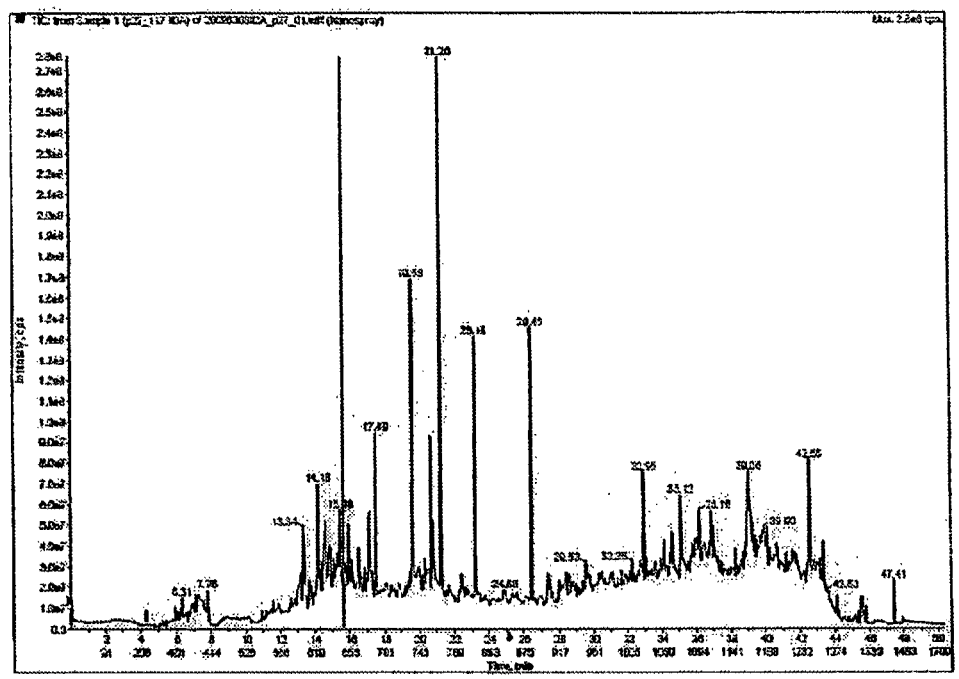
FIG. 1 shows the manner of selecting MRM transitions using PFTS in Example 1.
Figure 1:
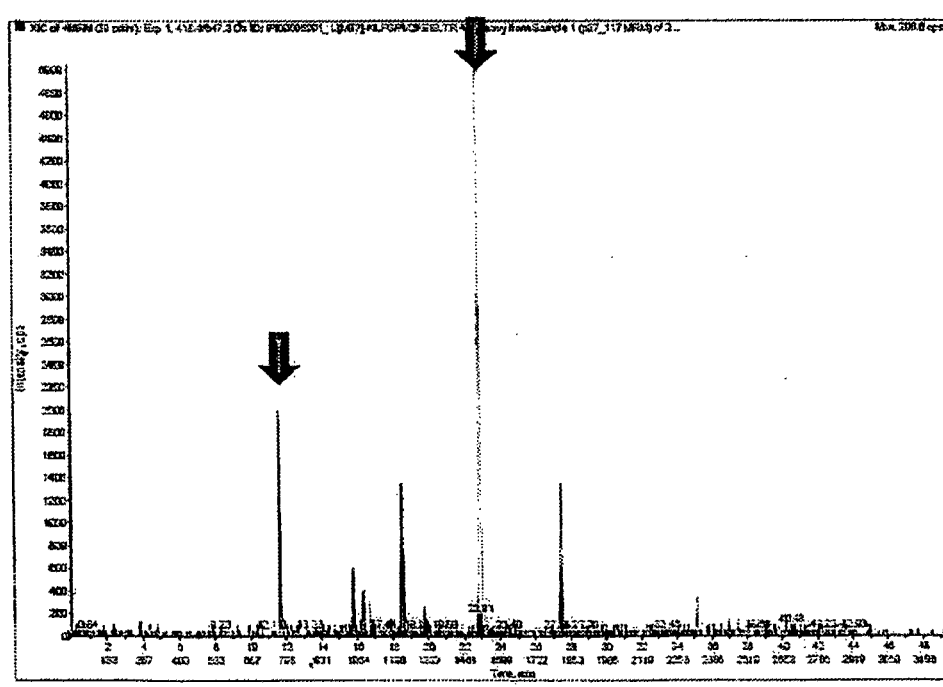

The method of the present invention identifies and quantifies target proteins in a sample containing plural kinds of proteins. A feature of this method is that the method comprises the following steps (A) to (D):

(A) a step of fragmenting a sample containing the target proteins, and labeling with a stable isotope X;

(B) a step of adding, to the sample obtained in step (A), known amounts of internal standards that are prepared by fragmenting a standard proteins that are identical to the target proteins, and labeling the fragmented standard proteins with a stable isotope Y;

(C) a step of placing the sample obtained in step (B) in an LC-MS/MS device, and performing multiple reaction monitoring (MRM) analysis using MRM transitions selected for the internal standards; and (D) a step of identifying, in the MRM chromatogram detected in step (C), peptides derived from the target proteins (target peptides) that show the same retention time as peptides derived from the internal standards (peptides of the internal standards), and quantifying the target protein in the test sample by comparing the peak areas of the peptides of the internal standards with the peak areas of the target peptides.

The test sample to be subjected to the method of the present invention is not particularly limited, and may be anything that contains two or more proteins. Examples of such samples include samples (biological samples) derived from microorganisms, plants, and animals (including humans). Specific examples thereof include blood, urine, saliva, hair, cells, cell tissues, and treated products thereof; and protein-containing samples prepared by gene recombination techniques.

Each of the steps is described below.

Step (A) (Fragmentation and Labeling)

In step (A), the target proteins are fragmented to each collection of peptides, and the fragmented target proteins are subsequently labeled with a stable isotope X.

To fragment the target proteins, for example, methods of digesting the target proteins with a proteolytic enzyme (protease) such as trypsin, and chemical cleavage methods, such as a method using cyanogen bromide, can be used. Digestion by protease is preferable. It is known that a given mole quantity of protein produces the same mole quantity for each tryptic peptide cleavage product if the proteolytic digest is allowed to proceed to completion. Thus, determining the mole quantity of tryptic peptide to a given protein allows determination of the mole quantity of the original protein in the sample. Absolute quantification of the target proteins can be accomplished by determining the absolute amount of the target protein-derived peptides contained in the protease digestion (collection of peptides). Accordingly, in order to allow the proteolytic digest to proceed to completion, reduction and alkylation treatments are preferably performed before protease digestion with trypsin to reduce and alkylate the disulfide bonds contained in the target proteins.

Subsequently, the obtained digest (collection of peptides) is subjected to labeling with a stable isotope X. Examples of stable isotopes X include $^1H$ and $^2H$ for hydrogen atoms, $^{12}C$ and $^{13}C$ for carbon atoms, and $^{14}N$ and $^{15}N$ for nitrogen atoms. Any isotope can be suitably selected therefrom. Labeling by a stable isotope X can be performed by reacting the digest (collection of peptides) with a reagent containing the stable isotope. Preferable examples of such reagents that are commercially available include mTRAQ (registered trademark) (produced by Applied Biosystems), which is an amine-specific stable isotope reagent kit. mTRAQ is composed of 2 or 3 types of reagents (mTRAQ-light and mTRAQ-heavy; or mTRAQ-D0, mTRAQ-D4, and mTRAQ-D8) that have a constant mass difference between them as a result of isotope-labeling, and that are bound to the N-terminus of a peptide or the primary amine of a lysine residue.

Step (B) (Addition of the Internal Standard)

In step (B), a known amount of internal standards are added to the sample obtained in step (A). The internal standards used herein are digests (collections of peptides) obtained by fragmenting proteins (standard proteins) consisting of the same amino acid sequence as the target proteins to be measured, and labeling the obtained digests (collections of peptides) with a stable isotope Y. The fragmentation treatment can be performed in the same manner as above for the target proteins. Labeling with a stable isotope Y can also be performed in the same manner as above for the target protein. However, the stable isotope Y used herein must be an isotope that has a mass different from that of the stable isotope X used for labeling the target protein digest. For example, in the case of using the aforementioned mTRAQ (registered trademark) (produced by Applied Biosystems), when mTRAQ-light is used to label digests of target proteins, mTRAQ-heavy should be used to label digests of standard proteins.

Step (C) (LC-MS/MS and MRM Analysis)

In step (C), the sample obtained in step (B) is first placed in an LC-MS/MS device, and then multiple reaction monitoring (MRM) analysis is performed using MRM transitions selected for the internal standards.

By LC (liquid chromatography) using the LC-MS/MS device, the sample (collections of peptides labeled with a stable isotope) obtained in step (B) is separated first by one-dimensional or multi-dimensional high-performance liquid chromatography.

Specific examples of such liquid chromatography include cation exchange chromatography, in which separation is conducted by utilizing electric charge difference between peptides; and reversed-phase chromatography, in which separation is conducted by utilizing hydrophobicity difference between peptides. Both of these methods may be used in combination.

Subsequently, each of the separated peptides is subjected to tandem mass spectrometry (MS/MS) by using a tandem mass spectrometer (MS/MS spectrometer) comprising two mass spectrometers connected in series. The use of such a mass spectrometer enables the detection of several fmol levels of a target protein. Furthermore, MS/MS analysis enables the analysis of internal sequence information on peptides, thus enabling identification without false positives. As the ionization method in mass spectrometry, an electrospray ionization method (ESI method), which is a soft ionizing method, is preferably used. In mass spectrometry, peptide-derived ions generated by various ionization methods are separated by an analyzer according to the mass. Examples of analyzers include magnetic sector mass spectrometers (Sector MS), quadrupole mass spectrometers (QMS), time-of-flight mass spectrometers (TOFMS), and Fourier transform ion cyclotron resonance mass spectrometers (FT-ICRMS); a combination of these spectrometers may also be used as the analyzer.

A feature of the method of the present invention is that to select the target peptides, multiple reaction monitoring (MRM) analysis is performed by using MRM transitions selected for the internal standards.

The selection of MRM transitions and selection of a target peptides using the MRM transitions can be performed by a method comprising the following steps (1) to (3):

(1) a step of fragmenting a standard proteins that are identical to the target proteins, and labeling the fragmented standard proteins with a stable isotope Y to prepare internal standards;

(2) a step of placing the internal standards obtained in step (1) in an LC-MS/MS device, and determining the peptide ion intensities corresponding to the peptides derived from the standard proteins; and (3) selecting two or more fragment ions that have high ionic intensity per peptide, determining the average intensities of two or more fragment ions, and selecting two or more peptides in descending order of the average intensity so as to select MRM transitions based on the peptides.

Steps (1) and (2) are carried out by digesting recombinant proteins (standard proteins) consisting of an amino acid sequence identical to that of the target proteins, with a protease such as trypsin, as described above, and subsequently labeling the digest with a stable isotope (such as mTRAQ heavy: labeled with IS); and conducting measurement by LC-MS in an automatic MS/MS solution mode using the labeled digest as a precursor-fragment transition selection standard (PFTS). The standard proteins are preferably recombinant proteins prepared based on a full-length cDNA library.

Subsequently, the obtained data are put through a search engine to perform spectral assignment and to list the peptides experimentally detected for each protein. The detected peptides are grouped for each protein, and three or more fragments having an m/z value larger than that of the precursor ion and three or more fragments with an m/z value of 500 or more are selected from each MS/MS spectrum in descending order of signal intensity on the spectrum. From these, two or more fragments are selected in descending order of intensities, and the average of the strength is defined as the expected sensitivity of the MRM transitions. When plural peptides is detected from one protein, two or more peptides with the highest sensitivity are selected as standard peptides using the expected sensitivity as an index. PFTS may consist of a single purified recombinant protein, or a mixture of plural proteins.

In the above method, the peptides with high expected sensitivity (the standard peptide selected for the standard protein) are preferably obtained with good reproducibility in order to prevent calculation error between columns in elution time (retention time) on the chromatogram (e.g., reversed-phase chromatogram) in liquid chromatography. More specifically, it is preferable that the chromatogram be normalized by using the elution time of two or more standard peptides, and that the elution time calculation error be controlled to within ±1 minute. This allows elution time-dependent MRM analysis (scheduled MRM analysis), and the number of proteins that can be quantified per analysis is drastically increased (approximately 400 proteins per run).

Step (D) (Quantification of the Target Protein in the Test Sample)

Step (D) comprises identifying, in the MRM chromatogram detected in step (C), peptides derived from the target proteins (target peptides) that show the same retention time as peptides derived from the internal standards (peptides of the internal standards), and quantifying the target protein in the test sample by comparing the peak areas of the internal standard peptides with the peak areas of the target peptides.

The target proteins can be quantified by utilizing a calibration curve of the standard proteins prepared beforehand.

The calibration curve can be prepared by the following method.

First, a recombinant protein consisting of an amino acid sequence that is identical to that of the target protein (a standard protein) is digested with a protease such as trypsin, as described above. Subsequently, precursor-fragment transition selection standards (PFTS) of a known concentration are individually labeled with two different types of stable isotopes (i.e., one is labeled with a stable isomer used to label an internal standard peptide (labeled with IS), whereas the other is labeled with a stable isomer used to label a target peptide (labeled with T)). Plural samples are produced by blending a certain amount of the IS-labeled PTFS with various concentrations of the T-labeled PTFS. These samples are placed in the aforementioned LC-MS/MS device to perform MRM analysis. The area ratio of the T-labeled PTFS to the IS-labeled PTFS (T-labeled PTFS/IS-labeled PTFS) on the obtained MRM chromatogram is plotted against the amount of the T-labeled PTFS to prepare a calibration curve (see FIG. 2).

With the use of this calibration curve, the absolute amount of the target protein contained in the test sample can be calculated.

In the method of the present invention, for the standard proteins corresponding to individual target proteins, calibration reference tables regarding MRM transitions, standard peptides derived from the standard proteins, and retention time, etc., of and the standard peptides in LC-MS/MS are preferably prepared beforehand. Such calibration reference tables are also preferably prepared beforehand for the standard proteins corresponding to individual target proteins. In this case, with reference to such calibration reference tables and calibration curves, steps (C) and (D) can be performed.

The calibration reference tables can be prepared by the method comprising the following steps:

(a) a step of fragmenting known amounts of standard proteins, and labeling with a stable isotope Y to prepare an internal standard;

(b) a step of placing the internal standard obtained in step (a) in an LC-MS/MS device, and performing multiple reaction monitoring (MRM) analysis using MRM transitions selected for the internal standard;

(c) a step of selecting, in the MRM chromatogram, at least two types of peptides from the detected peptides in descending order of sensitivity, and listing the peptides with the retention time thereof; and (d) a step of storing the list prepared in step (c) for use as a calibration reference table of the standard protein.

A library of standard proteins may be constructed by repeating steps (a) to (d) using at least two standard proteins, and preparing and storing calibration reference tables of the individual standard proteins. With the construction of such a library, the method of the present invention can determine absolute amounts of all of the proteins.

The present invention is directed to a method for measuring the amounts of proteins. However, synthesis and use of internal standard peptides corresponding to sites subjected to post-translational modification, such as phosphorylation, glycosylation, nitration, or citrullination, as peptides containing a post-translational modification site would enable measurement of the amounts of post-translationally modified target proteins. Furthermore, synthesis and use of internal standard peptides corresponding to peptides present in a living body would enable measurement of the amount of the peptide.

EXAMPLES

Example 1

Selection of MRM Transitions Using PFTS, and Preparation of Calibration Curve (1) Preparation of Recombinant Human Cyclin-Dependent Kinase Inhibitor Protein (Recombinant p27$^{Kip1}$) Using cDNA cDNA of p27$^{Kip1}$, which is a human cyclin-dependent kinase inhibitor protein, was incorporated into a pGEX-6P1 *E. coli* expression vector, and expressed as a GST-fusion protein in *E. coli*. Subsequently, the GST-fused p27$^{Kip1}$ was bound to Glutathione Sepharose, and the GST moiety was cleaved and eluted by treatment with PreScission Protease (produced by GE Healthcare). The thus-obtained recombinant p27$^{Kip1}$ was subjected to electrophoresis to measure the purity and the concentration.

(2) Enzyme Treatment (Digestion) of Recombinant p27$^{Kip1}$

The purified p27$^{Kip1}$ (600 ng) prepared above was dissolved in 100 μl of 100 mM Tris-HCl (pH 8.5) containing 7M guanidine hydrochloride, and incubated at 86° C. for 1 hour. After quenching, the resulting solution was mixed with an equal amount of 100 mM Tris-HCl (pH 8.5), and 0.1 μg of lysyl endopeptidase was added to perform incubation (37° C.) overnight.

Subsequently, 5 μl of 100 mM TCEP (tris(2-carboxyethyl) phosphine) was added, and the resulting mixture was subjected to reduction treatment (cleavage of disulfide bonds) at 56° C. for 30 minutes, after which the temperature was returned to room temperature, and 5 μl of 500 mM iodoacetamide was added. The resulting mixture was allowed to stand at room temperature for 30 minutes. After the mixture was diluted with 600 μl of purified water, 0.1 μg of trypsin was added, and incubation (37° C.) was performed overnight.

The obtained product (p27$^{Kip1}$ digest) was desalted using Sep-PAK C18 (produced by Japan Waters Co., Ltd.) (50 mg), and then subjected to centrifugal concentration.

(3) Stable Isotope Labeling

The dried product (p27$^{Kip1}$ digest) obtained by centrifugal concentration was re-dissolved in 40 μl of iTRAQ buffer (supplied with an iTRAQ reagent kit, produced by Applied Biosystems), and divided equally between two tubes. The solution in the tubes was treated with mTRAQ-light (mTRAQ-113: 1 unit) or mTRAQ-heavy (mTRAQ-117: 1 unit) at room temperature for 2 hours for labeling. After 100 μl of ultrapure water was added to each and mixed, the resulting mixtures were allowed to stand at room temperature for 1 hour, and then subjected to centrifugal concentration again. The concentrates were each re-dissolved in 20 μl of a 0.5% aqueous trifluoroacetic acid solution. The solutions thus obtained were used as stock samples (mTRAQ-113-labeled p27$^{Kip1}$ digest and mTRAQ-117-labeled p27$^{Kip1}$ digest: 10 pmol/μl each).

(4) LC-MS/MS Analysis

The p27$^{Kip1}$ digest labeled with mTRAQ-heavy (mTRAQ-117) (mTRAQ-117-labeled p27$^{Kip1}$ digest) was used as a precursor-fragment transition selection standard (PFTS). Twenty fmol of the digest was subjected to LC-MS/MS analysis (IDA mode) using a triple quadrupole mass spectrometry system (QTRAP 5500: produced by AB/Sciex) comprising a multi-dimensional chromatography HPLC system (Paradigm MS2, produced by Michrom BioResources, Inc.) and an autosampler (HTS-PAL, produced by HCT) connected to each other. The measurement was made using an L-column (produced by Chemicals Evaluation and Research Institute, filler diameter: 3 μm, inner diameter: 100 μm, column length: 15 cm) under the following conditions:
Mobile phase A: 0.1% formic acid/2 volume % aqueous methanol solution;
Mobile phase B: 0.1% formic acid/98% aqueous methanol solution;
Flow rate: 0.2 mL/min; and
Gradient: 5-95% mobile phase B for 30 minutes, 95-95% mobile phase B for 10 minutes, 95-5% mobile phase B for 1 minute, and 5-5% mobile phase B for 20 minutes.
FIG. 1A shows the results.

The obtained data were searched against human IPI version 3.1.6, which is a human protein database, using the database search engine MASCOT with ProteinPilot software (produced by Applied Biosystems).

Ten types of peptides with high expected sensitivity were selected from the peptides identified by the search. For each peptide, at least two types of fragment ions (MRM transitions) were selected. Using the selected MRM transitions, an mTRAQ-117-labeled p27$^{Kip1}$ digest, which was used as a sample, was actually subjected to MRM analysis again.

FIG. 1B shows the results. The obtained MRM chromatogram revealed that two types of peptides (indicated by arrows in FIG. 1B) can be detected with high sensitivity. With respect to the two types of peptides, high sensitivity MRM transition configuration information and retention time were recorded.

(5) Quantification of p27$^{Kip1}$

The mTRAQ-117-labeled p27$^{Kip1}$ digest and the mTRAQ-113-labeled p27$^{Kip1}$ digest prepared in (3) were mixed at the various ratios shown in Table 1, and 1 μl of each mixture was subjected to MRM analysis. The obtained MRM chromatograms were analyzed using MultiQuant (Applied Biosystems) to calculate the area ratio of the mTRAQ-113-p27$^{Kip1}$ digest to the mTRAQ-117-p27$^{Kip1}$ digest. The area ratio was plotted against the concentration of the mTRAQ-113-p27$^{Kip1}$ digest to prepare a calibration curve, which was stored as a MultiQuant calibration curve file (see FIG. 2).

TABLE 1

| mTRAQ-113-labeled p27$^{kip1}$ digest | TRAQ-113-labeled p27$^{kip1}$ digest | mTRAQ-117-labeled p27$^{kip1}$ digest |
|---|---|---|
| Blank | 0 | 10 |
| 1 fmol | 1 | 10 |
| 10 fmol | 10 | 10 |
| 100 fmol | 100 | 10 |

Figure 2:
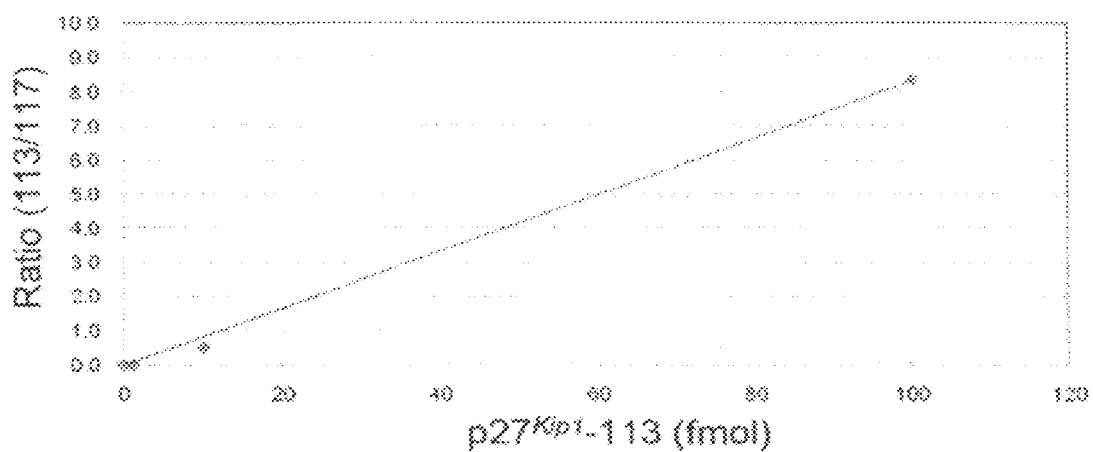
FIG. 2 shows a calibration curve prepared using PFTS. The calibration curve was obtained by calculating the area ratio of the mTRAQ-113 $p27^{Kip1}$ digest to the mTRAQ-117 $p27^{Kip1}$ digest, and plotting the calculation results relative to the concentration of the mTRAQ-113-$p27^{Kip1}$ digest.

FIG. 2 shows that the calibration curve is a straight line, thus confirming guaranteed reliability of the quantification.

Example 2

Absolute Quantification of Endogenous Proteins by the MRM Method (1) Preparation of Endogenous Proteins Using Skp2 protein-encoding gene-knockdown HeLa cells (Skp2 KD 1-2 cells and Skp2 KD 3-10 cells), and control cells (Mock) as starting materials, cell extracts were prepared. The Skp2 protein is a ubiquitination enzyme of p27$^{Kip1}$ (a human cyclin-dependent kinase inhibitor protein) prepared in Example 1.

Figure 3:
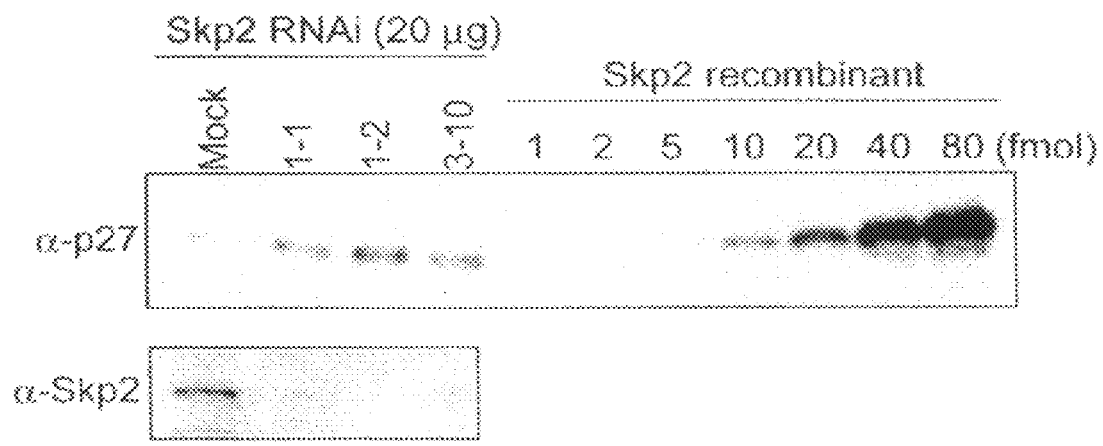
FIG. 3 shows the results obtained by preparing, as model cells, Skp2 knockdown HeLa cells (Skp2KD1-2 cells and Skp2KD3-10 cells), and measuring the amount of $p27^{Kip1}$ in the cells by western blotting using a recombinant $p27^{Kip1}$ as a control.

A decrease of the Skp2 protein in the cells by knockdown (FIG. 3, lower portion) and accumulation of p27$^{Kip1}$ thereby (FIG. 3, upper portion) were confirmed by western blotting. FIG. 3 shows the results. The amount of p27$^{Kip1}$ present in 20 μg of each extract was estimated. It was confirmed that the amount of p27$^{Kip1}$ in the control cells (Mock) was 3 fmol; the amount of p27$^{Kip1}$ in the knockdown cells (Skp2 KD 1-2 cells) was 20 fmol; and the amount of p27$^{Kip1}$ in the knockdown cells (Skp2 KD 3-10 cells) was 10 fmol.

(2) Enzyme Treatment (Digestion)

After 100 μg each of the cell extracts prepared above was subjected to TCA precipitation, the precipitates were washed with acetone. Subsequently, the precipitates were each dissolved in 100 μl of 100 mM Tris-HCl (pH 8.5) containing 7M guanidine hydrochloride, and incubated at 86° C. for 1 hour. Subsequently, after quenching, the resulting solutions were each mixed with an equal amount of 100 mM Tris-HCl (pH 8.5), and 1 μg of lysyl endopeptidase was added to perform incubation (37° C.) overnight.

Subsequently, 5 µl of 100 mM TCEP was added, and the resulting mixtures were subjected to reduction treatment at 56° C. for 30 minutes, after which the temperature was returned to room temperature, and 5 µl of 500 mM iodoacetamide was added. The resulting mixtures were allowed to stand at room temperature for 30 minutes. After the mixtures were each diluted with 600 µl of purified water, 1 µg of trypsin was added, and incubation (37° C.) was performed overnight.

The obtained products (digests) were desalted using Sep-PAK C18 (produced by Japan Waters, Co., Ltd.) (50 mg), and then subjected to centrifugal concentration.

(3) Stable Isotope Labeling

The dried products (digests) obtained by centrifugal concentration were re-dissolved in 20 µl of iTRAQ buffer (supplied with an iTRAQ reagent kit, produced by Applied Biosystems), and treated with mTRAQ-light (mTRAQ-113) (1 unit) at room temperature for 2 hours. After 100 µl of ultrapure water was added to each and mixed, the resulting mixtures were allowed to stand at room temperature for 1 hour and then subjected to centrifugal concentration again. The concentrates were each re-dissolved in 20 µl of a 0.5% aqueous trifluoroacetic acid solution, and 500 fmol of $p27^{Kip1}$-heavy (a mTRAQ-117-labeled $p27^{Kip1}$ digest) was added as an internal standard. The mixtures were desalted using a reversed-phase microcolumn, and subjected to centrifugal concentration.

(4) LC-MS/MS Analysis

Figure 4:
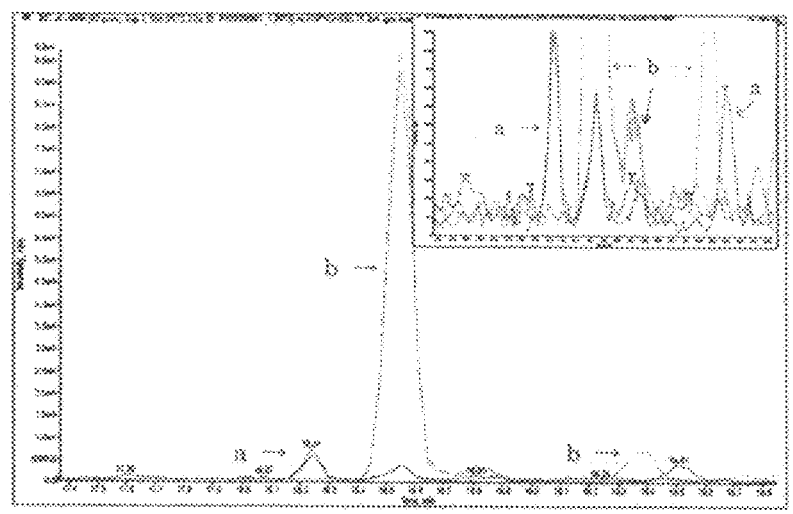
FIG. 4 shows the results of MRM analysis performed using $p27^{Kip1}$ MRM transitions (two types of peptides) prepared using PFTS (mTRAQ-117-labeled $p27^{Kip1}$ digest) and calibration curves in Example 1, and comparison of the amount (absolute amount) of $p27^{Kip1}$ present in Skp2 knockdown cells (Skp2KD1-2 cells and Skp2KD3-10 cells) with that in the control cells (Mock).
Figure 4:
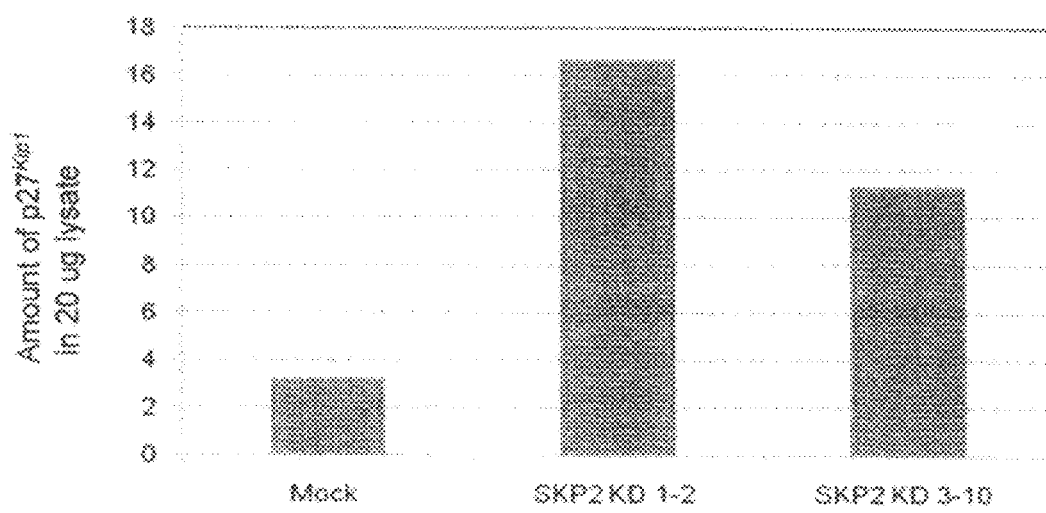

Using 2 µg each of the obtained digests (containing 10 fmol of $p27^{Kip1}$-heavy), MRM analysis was conducted. FIGS. 4A and 4B show the results. As is clear from FIG. 4A, sample-derived peaks that completely overlapped with internal standard ($p27^{Kip1}$-heavy)-derived MRM peaks were detected. The actual measurement data were read by MultiQuant (produced by Applied Biosystems) to calculate the area ratio, and the calibration curve obtained in step 4 was recalled to calculate the absolute amount of $p27^{Kip1}$-light ($p27^{Kip1}$-113) in the sample. As shown in FIG. 4B, the results show that the amount of $p27^{Kip1}$ in 20 µg of each of the cell extracts was such that the amount of $p27^{Kip1}$ in the control cells (Mock) was 3 fmol; the amount of $p27^{Kip1}$ in the knockdown cells (Skp2 KD 1-2 cells) was about 17 fmol; and the amount of $p27^{Kip1}$ in the knockdown cells (Skp2 KD 3-10 cells) was about 11 fmol, which were thus confirmed to be substantially the same as the estimates.

The invention claimed is:

1. A method for identifying and quantifying target proteins in a test sample containing plural kinds of target proteins in one analysis, the method comprising:
    (A) a step of fragmenting the sample containing the target proteins and labeling with a stable isotope X;
    (B) a step of obtaining collections of peptides by fragmenting standard proteins that are identical to the target proteins and by labeling the fragmented standard proteins with a stable isotope Y, the collections of peptides being internal standards;
    (C) a step of adding, to the sample obtained in step (A), known amounts of the internal standards obtained in step (B);
    (D) a step of placing the sample obtained in step (C) in an LC-MS/MS device,
        separating the sample by one-dimensional or multi-dimensional high-performance liquid chromatography,
        subjecting each of the separated peptides to tandem mass spectrometry by using a tandem mass spectrometer comprising two mass spectrometers connected in series, and
        performing multiple reaction monitoring (MRM) analysis using MRM transitions selected for the internal standards; and
    (E) a step of identifying, in the MRM chromatogram detected in step (D), peptides derived from the target proteins (target peptides) that shows the same retention time as peptides derived from the internal standards (peptides of the internal standards), and quantifying the target proteins in the test sample by comparing the peak areas of the peptides of the internal standards with the peak areas of the target peptides.

2. The method according to claim 1, wherein the MRM transitions are selected by a method comprising:
    (1) a step of fragmenting the standard proteins that are identical to the target proteins and labeling with the stable isotope Y to prepare internal standards;
    (2) a step of placing the internal standards obtained in step (1) in the LC-MS/MS device and determining the ionic intensities of peptides corresponding to the peptides derived from the standard proteins;
    (3) a step of selecting two or more fragment ions that have high ionic intensity per peptide, determining the average intensities of two or more fragment ions, and selecting two or more kinds of peptides in descending order of the average intensity so as to select the MRM transitions based on the peptides.

3. The method according to claim 1, wherein step (D) or (E) is performed based on a calibration reference table of the standard proteins.

4. The method according to claim 3, wherein the calibration reference table of each standard protein is prepared by a method comprising:
    (a) a step of fragmenting a known amount of the standard proteins and labeling with the stable isotope Y to prepare an internal standard;
    (b) a step of placing the internal standard obtained in step (a) in the LC-MS/MS device,
        separating the sample by one-dimensional or multi-dimensional high-performance liquid chromatography,
        subjecting each of the separated peptides to tandem mass spectrometry by using a tandem mass spectrometer comprising two mass spectrometers connected in series, and
        performing multiple reaction monitoring (MRM) analysis using the MRM transitions selected for the internal standard;
    (c) a step of selecting, in the MRM chromatogram, two or more kinds of peptides from the detected peptides in descending order of sensitivity, and listing the peptides with the retention time thereof;
    (d) a step of storing the list prepared in step (c) for use as the calibration reference table of the standard protein.

5. The method according to claim 4 wherein steps (a) to (d) are repeated using two or more standard proteins so as to prepare and store calibration reference tables of the standard proteins, thus constructing a standard protein library.

6. The method according to claim 2, wherein step (2) or (3) is performed based on a calibration reference table of the standard proteins.

7. The method according to claim 6, wherein the calibration reference table of each standard protein is prepared by a method comprising:
    (a) a step of fragmenting a known amount of the standard protein and labeling with the stable isotope Y to prepare an internal standard;
    (b) a step of placing the internal standard obtained in step (a) in the LC-MS/MS device, separating the sample by one-dimensional or multi-dimensional high-performance liquid chromatography, subjecting each of the separated peptides to tandem mass spectrometry by using a tandem mass spectrometer comprising two mass spectrometers connected in series, and performing multiple reaction monitoring (MRM) analysis using the MRM transitions selected for the internal standard;

(c) a step of selecting, in the MRM chromatogram, two or more kinds of peptides from the detected peptides in descending order of sensitivity, and listing the peptides with the retention time thereof;

(d) a step of storing the list prepared in step (c) for use as the calibration reference table of the standard protein.

8. The method according to claim 7, wherein steps (a) to (d) are repeated using two or more standard proteins so as to prepare and store calibration reference tables of the standard proteins, thus constructing a standard protein library.

9. The method according to claim 1, wherein the tandem mass spectrometer has an MRM analysis function.

10. The method according to claim 4, wherein the tandem mass spectrometer has an MRM analysis function.

11. The method according to claim 7, wherein the tandem mass spectrometer has an MRM analysis function.

12. The method according to claim 1, wherein the tandem mass spectrometer is a triple quadrupole mass spectrometry.

13. The method according to claim 4, wherein the tandem mass spectrometer is a triple quadrupole mass spectrometry.

14. The method according to claim 7, wherein the tandem mass spectrometer is a triple quadrupole mass spectrometry.

15. The method according to claim 1, wherein the standard proteins are full-length recombinant proteins.

16. The method according to claim 4, wherein the standard proteins are full-length recombinant proteins.

17. The method according to claim 7, wherein the standard proteins are full-length recombinant proteins.

* * * * *